(12) United States Patent
Dauvrin et al.

(10) Patent No.: US 6,379,938 B1
(45) Date of Patent: Apr. 30, 2002

(54) EPOXIDE HYDROLASE

(75) Inventors: Thierry Dauvrin, Couthuin; Pascale Deslee, Braives, both of (BE)

(73) Assignee: Puratos N.V., Groot-Bijgaarden (BE)

( * ) Notice: Subject to any disclaimer, the term of this patent is extended or adjusted under 35 U.S.C. 154(b) by 0 days.

(21) Appl. No.: 09/530,058

(22) PCT Filed: Oct. 23, 1998

(86) PCT No.: PCT/BE98/00160

§ 371 Date: Jul. 3, 2000

§ 102(e) Date: Jul. 3, 2000

(87) PCT Pub. No.: WO99/21972

PCT Pub. Date: May 6, 1999

(30) Foreign Application Priority Data

Oct. 24, 1997 (EP) .............................. 97870168

(51) Int. Cl.$^7$ .............................. C12P 4/18; C12N 9/14
(52) U.S. Cl. ....................... 435/158; 435/195
(58) Field of Search ................... 435/195, 158

(56) References Cited

U.S. PATENT DOCUMENTS 5,445,956 A    8/1995   Hammock et al. .......... 435/195

OTHER PUBLICATIONS

Martin Mischitz et al., Isolation of a Highly Enantioselective Epoxide Hydrolase From Rhodococcus sp. NCIMB 11216, *Biotechnology Letters*, vol. 17, No. 9, Sep. 1995, pp. 893–898.

Kenji Yamagishi et al., Enzymatic Preparation of D(–)–Tartaric Acid from cis–Epoxysuccinic Acid by Pseudomonas putida MC13037, *Animals of the New York Academy of Sciences*, vol. 799, 1996, pp. 784–785.

D(–)–tartaric acid preparation in high yield—by treating cis–epoxy: tartaric acid with cultured Pseudomonas microorganism, Database WPI, Section Ch, Week 9648, Sep. 24, 1996.

*Primary Examiner*—Charles L. Patterson, Jr.
(74) *Attorney, Agent, or Firm*—Knobbe, Martens, Olson & Bear, LLP (57) ABSTRACT

The present invention is related to an isolated and purified nucleotide sequence from microbial origin, encoding an epoxide hydrolase, the vector comprising said nucleotide sequence, the recombinant host cell transformed by said nucleotide sequence and the epoxide hydrolase amino acid sequence encoded by said nucleotide sequence and/or expressed by said recombinant host cell.

12 Claims, 4 Drawing Sheets

```
           10         20         30         40         50         60
           |          |          |          |          |          |
   1  GTCTTATCCT GGTAGCGCCC GTAATTTCGT GGGCTATCTT CGTTCTTCCG AGTGGATTGT
  61  GAGCACAATG CAACTGAACA ATGCGAACGA CAACACGCAG TTCCGGGCCC TGCTTTTCGA
 121  CGTGCAGGGG ACTCTGACAG ATTTCCGTTC CACACTCATC GAGCACGGCT TATCGATTCT
 181  CGGAGACAGA GTGGATCGAG AACTCTGGGA GGAATTGGTC GACCAATGGC GCGGCTGCTA
 241  TCGAGACGAG CTCGATTCCT TGGTCAAACA GGAGAAATGG CGCTCGGTCC GCGCCGTGTA
 301  CCGAGATTCT CTTATCAATC TTCTCGCAAA ATTCTCTGAC AGTTTCTGCG CCAACCTCGG
 361  CGAAGTGGAA TTGCTGACCG ATGGTTGGGA ACGTCTTCGG TCGTGGCCGG ACGTCCCCTC
 421  TGGATTGGAA CAGCTGCGGT CTAAGTACCT CGTCGCGGCA CTGACGAATG CGGACTTTTC
 481  TGCCATCGTC AACGTCGGGC GTAGCGCCAA ACTGCGTTC GACGCTGTTC TTTCAGCTCA
 541  ACTCTTTGA GCCTACAAGC CCCACCGGTC AACATATGAG GGAGCCGCGA CACTCCTGGG
 601  TATCGCTCCG TCAGAGATCC TCATGGTCGC CTCCCCATGCA ACGCCCACTG AAGCGGCGCG
 661  GGAAGTGGGA GCCGGCACAG CGTACGTCAG ACGTTTTGGT TTTCTTGGT CGACGGGGCG
 721  AACCGAGGAC GTTCCCGATG GACTCGGTGG AACTGCCGGT GCATTCCCCG GTGAACTGGC
 781  TGATCAGCTG GGCTGCCCAC TTCGGTGCCT GCAATTCCCG GCATTCCCCG TCAGTCACGG
 841  GGTTCCACGC GTCCCTTGTT TTCGGTGCCT GCATTCCCCG TGACGGCAAT CTGGAGTTTT
 901  GGAATGCAGG CTCTGCTCTG TGCCCAGGAT TTCAGGCGCT TCCCAGGCAA GATGACTCCG
 961  TGCAGCGTAG AGGGCGCCTT CGTTCATGAG TTCCTGTGCG GGGGTGTGA ACGGTGGCGC
1021  CCTACAGACA GCGGCGATGT GAAGGTAGGA CTCCGGGACG AATGCGGTGC AATCCGCTGA
1081  CGACCTGCCG TGCCGATGGC GCCCAGGAGG GCCCGGGTGG ACGGCATGAC AGCCTGTCCG GCTTCGACAC
1141  GCACCATCGG CAGGATCGAG GTCCGGTGGG CAACTTCGGC GACGATGGTG TCCTCGCTGG GACGAATCA
1201  CGCTGGGCGAG AACCTCGTCG ACCAGCGTTC GCATCAATGA TTTCCGGACG GCTTCGACAC GAGACAATCA
1261  ATCGGAAGCC GGACAGTTCC ACCGGGTAAA TTTCCGGACG TCCTCGCTGG GACGAATGA
1321  GCCCGGACAT GAGGATCAGC GGTTGACTTT CCAGTGCCAC AACCTC
```

```
  1 MQLNANDNTQFRALLFDVQGTLTDERSTL
 31 IEHGLSILGQEELWELVDQHWNPDRGCYRSGL
 61 ELDSLVKQEKVRRLLTDADEVYRDSLINLLAKFS
 91 DSFCATSKYLVAALFGAYKPHRSAIVGRSAKLLGIA
121 EQLRSAQLVAALTNADESAIVYEGAATLLGIVRRP
151 WDAVLSMVASHAYDLEAAREVGDSISELADQ
181 PSEILMVASHAYDLEARFDFLVDSISELADQ
211 LEYGPTGRTEDVPDGRFDFLV
241 LGCPRLGGTAGID
```

EPOXIDE HYDROLASE

This is the U.S. National Phase under 35 U.S.C. §371 of International Application PCT/BE98/00160, filed Oct. 23, 1998, which claims priority of European Application EP 97870168.8, filed Oct. 24, 1997.

FIELD OF THE INVENTION

The present invention relates to epoxide hydrolase nucleotidic and amino acid sequences and to their use in the enantiomeric hydrolysis of epoxides.

BACKGROUND OF THE PRESENT INVENTION

Epoxides

Epoxides are used as chiral building blocks in the organic synthesis of fine chemicals, especially enantiomerically pure compounds. They are reactive molecules as their ring may be easily open to give a broad range of products. For this reason, they occupy a place of importance among the precursors of pharmaceuticals and speciality chemicals. Some chemical methods exist for preparing them from optically active precursors, but no efficient asymmetric syntheses involving asymmetrisation or resolution methods are known with the exception of the Sharpless-epoxidation method, which is limited to allylic alcohols (Katsuki et al., *J. Am. Chem. Soc.* 102, p. 5974 (1980)). The use of biological reactions to perform epoxides synthesis has also been investigated (see for example the review of de Bont J. A. M., *Tetrahedron: Asymmetry* 4, p. 1331 (1993)).

Other epoxides, like halogenated aliphatic epoxides, are potential pollutants that are released into the environment from various industrial sources or that may be formed during the transformation of other synthetic chemicals. For example, epichlorohydrin (3-chloro-1,2-epoxypropane) is a widely used industrial chemical that is well recognised as mutagenic and carcinogenic.

Epoxide Hydrolases

Epoxide hydrolases (EC3.3.2.3.) are hydrolytic enzymes which catalyse the opening of an epoxide ring converting their substrate to the corresponding diol. One of their most interesting properties is that they are generally highly regio- and enantioselective, allowing the preparation of pure enantiomers.

Epoxide hydrolases have been studied in a variety of organisms. The best studied are those from mammals. They are found mainly in liver, testis, kidney, ovary and lung. They have been intensively characterised because of their involvement in the metabolism of xenobiotics (detoxification of cytotoxic, mutagenic and carcinogenic intermediates) (Seidegard et al., *Biochemica et Biophysica Acta* 695, p. 251 (1983)).

Epoxide hydrolases have been also described in other higher eukaryotes like plants and insects.

Due to their low availability, enzymes from such sources are not of practical value for large-scale processes. The microbial world represents a suitable alternative due to the possibility of cultivating micro-organisms on a large-scale. The use of whole cells to perform the biotransformation of epoxides has been investigated. Microbial epoxide hydrolases have been already described in a variety of micro-organisms. Some examples of such descriptions are summarised hereafter:

*Aspergillus niger* LPC521 and *Beauvaria sulfurescens* ATCC7159 possess enantiocomplementary epoxide hydrolases that hydrolyse the two racemic forms of styrene epoxide (Pedragosa-Moreau et al., *J. Org. Chem.* 58, p. 5533 (1993)).

*Diplodia gossipina* ATCC16391 catalyses the kinetic resolution of racemic indene oxide into 1(S), 2(R) indene oxide (Zhang et al., *J. Ferment. Bioeng.* 80, p. 244 (1995)).

Epichlorhydrin (3-chloro-1,2-epoxypropane) is transformed in (R)-3-chloro-2-propanol by a epoxide hydrolase characterised in Corynebacterium sp strain N-1074 (Nakamura et al., *J. Bact.* 174, p. 7613 (1992)). A similar enzyme has been purified from Pseudomonas sp. strain AD1 (Jacobs et al., *Eur. J. Biochem.* 202, p. 1217 (1991)).

An epoxide hydrolase that catalyses the asymmetric hydrolysis of various racemic epoxides in chiral epoxides and diols has been isolated from Rhodococcus sp. NCIMB 11216 (Mischitz et al., *Biotechnol. Lett.* 17, p. 893 (1995)).

A strain of Flavobacterium sp. is able to convert trans-1-epoxysuccinic acid in mesotartaric acid (Martin et al., *Biochem. J.* 70, p. 405 (1955)).

The epoxide hydrolase of Nocardia tartaricans catalyses the hydrolysis of cis-epoxysuccinate to give L(+)tartaric acid (Patentschrift DE 2605921). The same reaction could be performed by some other micro-organisms like Achromobacter, Alcaligenes (U.S. Pat. No. 3,957,579), *Acinetobacter tartarogenes, Agrobacterium aureum, Agrobacteriuzn viscosum, Rhizobium validum,* Pseudomonas sp. (Offenlegungsschrift DT 2619311).

A characteristic common to all these examples is the use of whole cells or whole crude extracts of the cells to perform the reaction. The enzyme can be liberated either by breaking the cells by physical disruption or by permeabilising the cell wall and/or the cell membrane by the use of detergents.

Tartaric Acid

Tartaric acid is used by the food industry for various applications (additive in soft drinks, food preservative, raw material for the synthesis of emulsifiers, . . . ). It is possible to synthesise chemically the tartaric acid starting from maleic acid but this process gives a racemic product composed of L(+)-tartaric acid and D(+)-tartaric acid. In food, only the L(+) form of tartaric acid is authorised as the D(+) is considered as harmful for human health.

L(+)-tartaric acid is produced naturally as a by-product during wine fermentation, but the supply of this compound is variable from year to year as it is very dependant of the climate.

The enzymatic hydrolysis of cis-epoxysuccinate by a cis-epoxysuccinate hydrolase allows the obtention of the only L(+) form of tartaric acid. This biotransformation would thus represent a valuable alternative for the production of L(+) tartaric acid.

State of the Art

Rink et al. (*J. of Biological Chemistry* 272 (23) (Jun. 6, 1997)) describe the primary structure and catalytic mechanisms of the epoxide hydrolase from the strain *Agrobacterium radiobacter* AD1.

Murdiyatmo et al. (*Biochemical Journal Vol.* 284, pp. 87–93 (May 1992)) describe the molecular biology of the 2-haloacid-halidohydrolase-IVa from *Pseudomonas cepacia* MBA4.

Mischitz et al. (*Biotechnology Letters* No. 17(9), pp. 893–898 (1995)) describe the isolation of a highly enantioselective epoxide hydrolase from a strain of Rhodococcus sp. having a molecular weight of 33–35000 kD and obtained from gel filtration chromatography SDS page. Said document states that the optimum temperature of the epoxide hydrolase is 30° C. However, said document never describes the amino acid sequence of said enzyme and the possible nucleotide sequence encoding said enzyme.

Yamagishi & Cho (*Annals of New York Academy of Sciences* Vol. 799, pp. 784–785 (1996)) describe the enzymatic preparation of tartaric acid from cis-epoxysuccinic acid by the strain *Pseudomonas putida* MCI3037.

A similar preparation of tartaric acid is described in the Japanese patent application JP-08245497 by treating cis-epoxytartaric acid with a culture of a Pseudomonas microorganism.

SUMMARY OF THE INVENTION

The present invention is related to a isolated and purified nucleotide sequence from *Rhodococcus rhodochrous*, preferably a strain having the deposit number LMGP-18079, encoding an epoxide hydrolase.

According to the invention, said nucleotide sequence (genomic DNA, CDNA, RNA) presents more than 50%, preferably more than 70%, more preferably more than 90% homology with the sequence SEQ ID NO 5 described hereafter.

According to a preferred embodiment of the present invention, said isolated and purified nucleotide sequence corresponds to the nucleotide sequence SEQ ID NO 5 or a portion thereof encoding a peptide having an epoxide hydrolase activity.

It is meant by "a portion of the nucleotide sequence SEQ ID NO 5", a fragment of said sequence SEQ ID NO 5 having more than 100 nucleotides of said nucleotide sequence and encoding a protein characterised by an epoxide hydrolase enzymatic activity similar to the epoxide hydrolase activity of the complete amino-acid sequence SEQ ID NO 6.

Preferably, said portion has an epoxide hydrolase enzymatic activity of more than 80% of the epoxide hydrolase enzymatic activity of the amino acid sequence SEQ ID NO 6, preferably has an epoxide hydrolase enzymatic activity corresponding to the one of the amino acid sequence corresponding to SEQ ID NO 6.

Another aspect of the present invention is related to a recombinant nucleotide sequence comprising, operably linked to the nucleotide sequence according to the invention and above-describes, one or more adjacent regulatory sequence(s), preferably originating from homologous micro-organisms.

However, said adjacent regulatory sequences can also be originating from heterologous micro-organisms.

These adjacent regulatory sequences are specific sequences such as promoters, secretion and termination signal sequences.

Another aspect of the present invention is related to the vector comprising the nucleotide sequence(s) according to the invention, possibly operably linked to one or more adjacent regulatory sequence(s) originating from homologous or from heterologous micro-organisms.

It is meant by "a vector", any biochemical construct which can be used for the introduction of a nucleotide sequence (by transduction or transfection) into a cell. Advantageously, the vector according to the invention is selected from the group consisting of plasmids, viruses, phagemides, liposomes, cationic vesicles or a mixture thereof. Said vector may comprise already one or more of the above-described adjacent regulatory sequence(s).

Preferably, said vector is a plasmid having the deposit number LMBP-3666.

The present invention is also related to the host cell, preferably a recombinant host cell, transformed by the nucleotide sequence or the vector according to the invention above-described.

It is meant by "a host cell transformed by the nucleotide sequence or the vector according to the invention", a cell having incorporated said nucleotide sequence or said vector and which does not comprise naturally said nucleotide sequence or said vector.

Preferably, said host cell is also capable of expressing said nucleotide sequence or said vector and allows advantageously the production of an amino acid sequence encoded by said nucleotide sequence or by said vector. The isolated and purified nucleotide sequence according to the invention can be either integrated into the genome of the selected host cell or present on a episomal vector in said host cell.

Advantageously, the recombinant host cell according to the invention is selected from the group consisting of the microbial world, preferably bacteria or fungi, including yeast.

Preferably, said recombinant host cell is modified to obtain an expression of the epoxide hydrolase enzyme at high level.

Preferably, said expression at high level is obtained by the use of adjacent regulatory sequences being capable of directing the overexpression of the nucleotide sequence according to the invention in the recombinant host cell.

Another aspect of the present invention is related to the isolated and purified (from possible contaminants) epoxide hydrolase amino acid sequence encoded by the isolated and purified nucleotide sequence and/or expressed by the recombinant host cell according to the invention.

Figure 5:
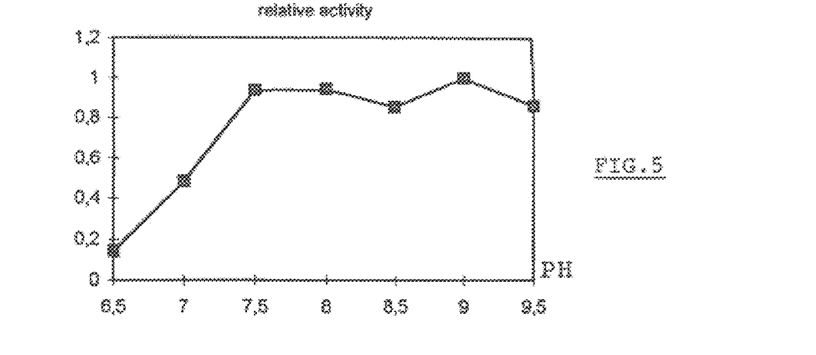
FIG. 5 represents the relative enzymatic activity of the enzyme according to the invention.

The isolated and purified epoxide hydrolase amino acid sequence according to the invention is also characterised by an advantageous pH activity profile having a high enzymatic activity (more than 80% of the optimum enzyme activity) between 7.0 and 10, preferably between 7.5 and 9.5 (see FIG. 5).

Advantageously, said isolated and purified epoxide hydrolase has a molecular weight comprised between 26 and 30 kD, preferably a molecular weight about 28 kD (theoretical molecular weight 28,136 kD).

Said epoxide hydrolase amino acid sequence or peptide is extra-cellular or intra-cellular expressed and/or secreted by the recombinant host cell according to the invention.

According to a preferred embodiment of the present invention, the isolated and purified epoxide hydrolase amino acid sequence presents more than 5%, preferably more than 70%, more preferably more than 90% homology with the amino acid sequence SEQ ID NO 6.

According to another preferred embodiment of the present invention, the isolated and purified epoxide hydrolase amino acid sequence has the amino acid sequence of SEQ ID NO 6 or a smaller portion of said amino acid sequence (of more than 50 amino-acids, preferably more than 100 amino-acids), which has at least more than 80% of the epoxide hydrolase activity of the complete amino acid sequence SEQ ID NO 6, preferably more than 95% of the epoxide hydrolase activity of the complete amino acid sequence SEQ ID NO 6. In other words, the isolated and purified epoxide hydrolase amino acid sequence according to the invention can be deleted partially while maintaining its enzymatic activity, which can be measured by methods well known by the person skilled in the art. Said isolated and purified epoxide hydrolase or its portion has a molecular weight lower than 30 kD, preferably about 28 kD or lower.

An epoxide hydrolase of interest is identified via an enzymatic assay not critical for the present invention, such as the hydrolysis of cis-epoxysuccinate in L(+)tartaric acid.

To perform this assay the micro-organism is cultivated in an appropriate medium to produce the enzyme of interest (e.g. by induction with cis-epoxysuccinate). The whole cells or the culture medium are separately tested for the enzymatic activity.

Once an epoxide hydrolase has been identified, the DNA sequence encoding such epoxide hydrolase may be obtained from the micro-organisms which naturally produce it or from the recombinant cells according to the invention by culturing said micro-organisms or said cells in the appropriate medium to induce and produce the enzyme (epoxide hydrolase) of interest, isolating the desired epoxide hydrolase using known methods such as column chromatography, and determining the "active portion" of the amino acid sequence of the purified enzyme.

The DNA sequence encoding the epoxide hydrolase is obtained from a gene library of the micro-organism from which the epoxide hydrolase has been purified.

According to the present invention an oligonucleotide probe was derived from a portion of the amino acid sequence determined above. This oligonucleotide probe was used to screen a partial gene library of the micro-organism from which the epoxide hydrolase of interest has been purified. A 8 kb BamHI-EcoRI genomic DNA fragment containing the epoxide hydrolase-encoding sequence has been obtained as an insert in the plasmid vector pBlueScript SK(+). The resulting plasmid was designated pREHBE.

The size of the insert of the plasmid pREHBE has been reduced to 1.4 kb by digestion with the restriction enzymes SphI and XhoI and insertion in appropriate restriction sites of the plasmid vector pBluescript SK(+). The resulting plasmid was designated pREHXS and has been deposited (in *E. coli* DH10B) at the LMBP (BCCM/LMBP Plasmid collection, Laboratorium voor Moleculaire Biologie, Universiteit Gent, K. L. Ledeganckstraat, 35, B-9000 Gent) under the accession number LMBP-3666. The entire sequence of the insert was determined by manual sequencing using techniques well known by the person skilled in the art.

The expression constructs as described above allowed their expression in a *Escherichia coli* host. According to the present invention, said *Escherichia coli* host containing the plasmid pREHXS is cultivated in an appropriate medium (e.g. LB medium) and containing the appropriate antibiotic to allow the continuous presence of the plasmid in host cells, then the cells are collected and the epoxide hydrolase activity of the enzyme is determined. It is in the scope of the present invention not to limit the expression of the epoxide hydrolase gene to *Escherichia coli*. According to the present invention, the DNA fragment encoding the epoxide hydrolase could be advantageously expressed in bacteria or fungi, including yeast. To permit the expression of the gene of interest in such hosts, the DNA sequence encoding the epoxide hydrolase could eventually be operably linked to DNA sequences that will permit the (over)expression in the chosen host (e.g. promoters, terminators, UAS, . . . sequences).

The DNA sequence encoding the epoxide hydrolase is preferably modified to allow the secretion (extra cellular expression) of the epoxide hydrolase in the host cell culture medium. Such modification is usually done by adding a DNA sequence encoding a leader sequence that is recognised by the secretion machinery of the chosen host and allows the recovery of the epoxide hydrolase in its culture medium.

The present invention also provides the conditions (culture medium, temperature, . . . ) for the cultivation of the host selected for the expression of the epoxide hydrolase.

A last aspect of the present invention is related to the use of the recombinant host cell according to the invention or the isolated and purified epoxide hydrolase amino acid sequence according to the invention for the hydrolysis of an epoxide, preferably the cis-epoxysuccinate.

The new enzyme according to the invention can be advantageously used to hydrolyse epoxide rings found in epoxide substrates. Known examples of epoxides are styrene epoxides, octene epoxides, naphthalene epoxides, phenantrene epoxides, benzene oxide, estroxide, androstene oxide, epichlorhydrin, and cis-epoxysuccinate. Preferably, the epoxide hydrolase according to the invention can be used for the hydrolysis of the cis-epoxysuccinate but does not allow an hydrolysis of the epoxide substrate epichlorhydrin.

The enzyme according to the invention can be used under several forms: the cells can be used directly after cultivation with or without permeabilisation, and the enzyme could be used as a cell extract (i.e. portions of the host cell which has been submitted to one or more centrifugation and extraction step(s)) or as a purified protein. Any of the form above-described can be used in combination with another enzyme under any of the above-described forms. Furthermore, the enzyme can be recovered from the culture medium of a host cell expressing and secreting the epoxide hydrolase outside the cells. In this case, the enzymatic preparation can be used either as a crude preparation or as a partially or totally purified preparation in combination or not with one or several other enzyme(s).

These whole cells, cell extracts, cell-free extracts or purified epoxide hydrolase can be fixed (immobilised by any conventional means on a solid support such as a chromatography column) to allow a continuous hydrolysis of the epoxide substrate or to allow a recycling of the enzymatic preparation (whole cells, cell extracts, cell-free extracts, totally or partially purified epoxide hydrolase, etc.).

The invention will be described in further details in the following examples by reference to the enclosed drawings, which are not in any way intended to limit the scope of the invention as claimed.

BRIEF DESCRIPTION OF THE DRAWINGS

FIG. 3 shows the nucleotide sequence of the *Rhodococcus rhodochrous* LMGP-18079 cis-epoxysuccinate hydrolase gene and its flanking regions.

EXAMPLES

Example 1

Partial Purification of an Epoxide Hydrolase Strain

*Rhodococcus rhodochrous* LMGP-18079 is routinely maintained on agar slants containing 0.4% glucose, 0.4% yeast extract, 1% malt extract and 2% agar.

Determination of the Cis-epoxysuccinate-hydrolase Activity

The enzymatic reaction is performed at 37° C. in a final volume of 9.3 ml that contains the following components: 0.7 ml of 0.1N Tris.HCl buffer pH 8.0, 2.6 ml of a 1.14% Triton X-100 solution, 5.0 ml of a 30% sodium cis-epoxysuccinate solution and 1.0 ml of the cell suspension. The reaction is stopped by diluting the mixture between 100 and 500 times with $H_2O$ acidified to pH 2.2 with $H_3PO_4$.

The amount of L-tartaric acid formed during the reaction is determined by HPLC at room temperature on a Vydac C18 column (cat no. 201HS3410) with a flow rate between 400 and 600 µl/min and a sample volume of 20 µl. The solvent is the same as the one used to dilute the samples. The detection of cis-epoxysuccinate and tartaric acid occurs at 210 nm.

Activity is expressed as the amount of L(+)-tartaric acid formed in a day by 1 gram of dried cells.

For rapid qualitative analysis of soluble fractions containing the enzyme, the enzymatic reaction is performed at 37° C. in a final volume of 1 ml in 10 mM Tris-HCl pH 8.0 with 0.5 ml sodium cis-epoxysuccinate (30%) as substrate.

Cultivation of the Strain and Induction of the Cis-epoxysuccinate-hydrolase Activity The standard medium has the following composition (in g/l): propylene glycol 10, Yeast extract 2, $KH_2PO_4$ 2, $Na_2HPO_4.2H_2O$ 2.2, $(NH_4)_2SO_4$ 3, $CaCl_2.2H_2O$ 0.03, $MnSO_4.H_2O$ 0.003, $MgSO_4.7H_2O$ 0.1, $FeSO_4.7H_2O$ 0.01. The pH is adjusted to 7.0 and the culture is incubated at 30° C. with agitation. The cis-epoxysuccinate hydrolase activity is induced by adding after 24 hours 10 g/l of cis-epoxysuccinate. Cells are collected by centrifugation and stored at −20 ° C. until use.

Partial Purification of the Cis-epoxysuccinate Hydrolase
1. Obtention of the Cell-free Extract About 26 g of frozen cells are suspended in 35 ml of potassium phosphate buffer 50 mM pH 7.2 containing 5 mM DTT, 0.5 mM PMSF, 5 mM EDTA and 2 µg/ml pepstatine.

The cells are disrupted with glass beads using a Braun MSK homogeniser cooled by liquid $CO_2$.

The homogenate is first centrifuged at 7000 rpm in the SS34 rotor of the Sorvall RC5B centrifuge. The resulting pellet is re-extracted with 50 ml of cold buffer and centrifuged again. The two combined supernatants are then centrifuged for 20 min at 16000 rpm in the same rotor at 4° C. A final centrifugation step of 60 min at 38000 rpm in the rotor A641 of the Beckman LB-70 centrifuge gives the cell-free extract.

The extract (138 ml) is dialysed overnight at 4° C. against 2 l of potassium buffer 50 mM pH 7.2 containing 1M $(NH_4)_2SO_4$, 2.5 mM DTT and 2.5 mM EDTA.

2. Chromatography on Phenyl-Sepharose

After dialysis the extract is loaded on a 30 ml Phenyl Sepharose (Pharmacia Biotech) column equilibrated with the dialysis buffer. After washing with the same buffer, the bound proteins are eluted at 3 ml/min with 240 ml of a 1M–0M $(NH_4)_2SO_4$ linear gradient in the same buffer. Fractions of 3 ml are collected and assayed for cis-epoxysuccinate-hydrolase activity.

Active fractions are pooled and dialysed against 50 mM potassium phosphate buffer pH 7.2 containing 2.5 mM EDTA and 2.5 mM DTT.

3. Chromatography on Q-Sepharose

The dialysate of step 2 is applied on a 10 ml Q-Sepharose (Pharmacia Biotech) column equilibrated with the dialysing buffer. After washing with the same buffer, the bound protein are eluted from the column at 1 ml/min with a 80 ml linear gradient of NaCl (0–0.5M) in the same buffer. Fractions of 1 ml are collected and assayed for cis-epoxysuccinate-hydrolase activity.

4. Chromatography on MonoQ

About 1/10 of the pooled active fractions of step 3 is diluted 2.7-fold with 50 mM potassium phosphate buffer pH 7.2 containing 2.5 mM EDTA and 2.5 mM DTT and loaded on a MonoQ HR 5/5 column (Pharmacia Biotech). The proteins are eluted from the column with a linear gradient of NaCl (0–0.5M) in the same buffer at 0.25 ml/min. Fractions of 0.25 ml are collected and assayed for cis-epoxysuccinate-hydrolase activity.

5. Electrophoresis on SDS-PAGE

25 µl of the fractions collected from the MonoQ column are applied on a 12.5% acrylamide SDS gel (Mini-PROTEAN II Electrophoresis system—Bio-Rad). Proteins on the gel are visualised by staining with Coomassie Blue.

Example 2

Determination of the Amino Acid Sequence of the Cis-epoxysuccinate Hydrolase

General procedures were followed to perform the N-terminal sequencing of the protein after electrophoresis on a SDS-polyacrylamide gel and electroblotting on a PVDF Immobilon-P membrane (Millipore). An automatic 477A Protein Sequencer coupled to a HPLC 120A Analyser (Applied Biosystem) was used.

For the determination of the sequence of internal fragments, the protein was first digested on the membrane with trypsine. The resulting peptides were separated by reverse phase chromatography on HPLC, and subjected to N-terminal sequencing as above.

```
N-terminal :              MQLNNANDNTQF   SEQ ID NO 1
1st internal peptide :    SWPDVPSGLEQLR  SEQ ID NO 2
2nd internal peptide :    RPLEYGPTGR     SEQ ID NO 3
```

Example 3

Identification of the Cis-epoxysuccinate-hydrolase Gene
1. Design of the Oligtonucleotide Probe Based on the N-terminal sequence of the protein (SEQ ID NO 1) a oligonucleotide labelled with digoxigenine has been synthesised. This oligonucleotide has the following sequence:

5' AAYAAYGCNAAYGAYAAYAC 3' SEQ ID NO 4 Y represents either C or T, N represents any of the four bases.

2. Hybridisation of the Oligonucleotide with Total *Rhodococcus rhodochrous* DNA
2.1. Isolation of Genomic DNA

*Rhodococcus rhodochrous* LMGP-18079 strain is cultivated overnight in 200 ml of LBroth à 37° C. After collection by centrifugation, cells are washed for 30 minutes at 80° C. with TE buffer (Tris-HCl 10 mM, EDTA 1 mM, pH 8.0), centrifuged again, resuspended in 15 ml of TSE buffer (Tris-HCl 50 mM, Sucrose 200 mM, EDTA 1 mM, pH 8.0) with 120 mg of lysozyme and incubated for 2 hours at 37° C. before addition of 1.5 ml of 250 mM EDTA, pH 8.0. The mixture is further incubated for 60 minutes. After addition of 1 ml of STE (SDS 20%, Tris-HCl 50 mM, EDTA 20 mM, pH 8.0), the mixture is incubated for 30 minutes at 55 ° C.

DNA is separated from the contaminating material by successive extractions with phenol and phenol-chloroform and by precipitation with ethanol.

2.2. Southern Blotting

About 6 µg of *Rhodococcus rhodochrous* DNA are digested with various restriction enzymes (EcoRI, BamHI, SalI, PstI) or by a combination of these restriction enzymes (EcoRI+BamHI, EcoRI+PstI, EcoRI+SalI, BamHI+SalI, BamHI+PstI, SalI+PstI). The samples are loaded on a 20×20 cm 1% agarose gel and run overnight at 40 volts in buffer TAE (Tris-Acetate 40 mM, EDTA 1 mM, pH 8.0).

After migration the DNA the gel is treated and transferred on a Hybond N+ membrane (Amersham) as recommended by the manufacturer. Hybridisation buffers and detection conditions were those recommended in the digoxigenine detection kit (Boehringer Mannheim). Prehybridisation was performed overnight at 42° C. Hybridisation occurred at 42° C. for 6 hours. The washing conditions were the following: 2×5 minutes at room temperature with 2×SSC, 0.1% SDS, 2×15 min at 42° C. with 0.5×SSC 0.1% SDS and 2×15 min at 42° C. with 0.1×SSC 0.1% SDS.

Figure 1:
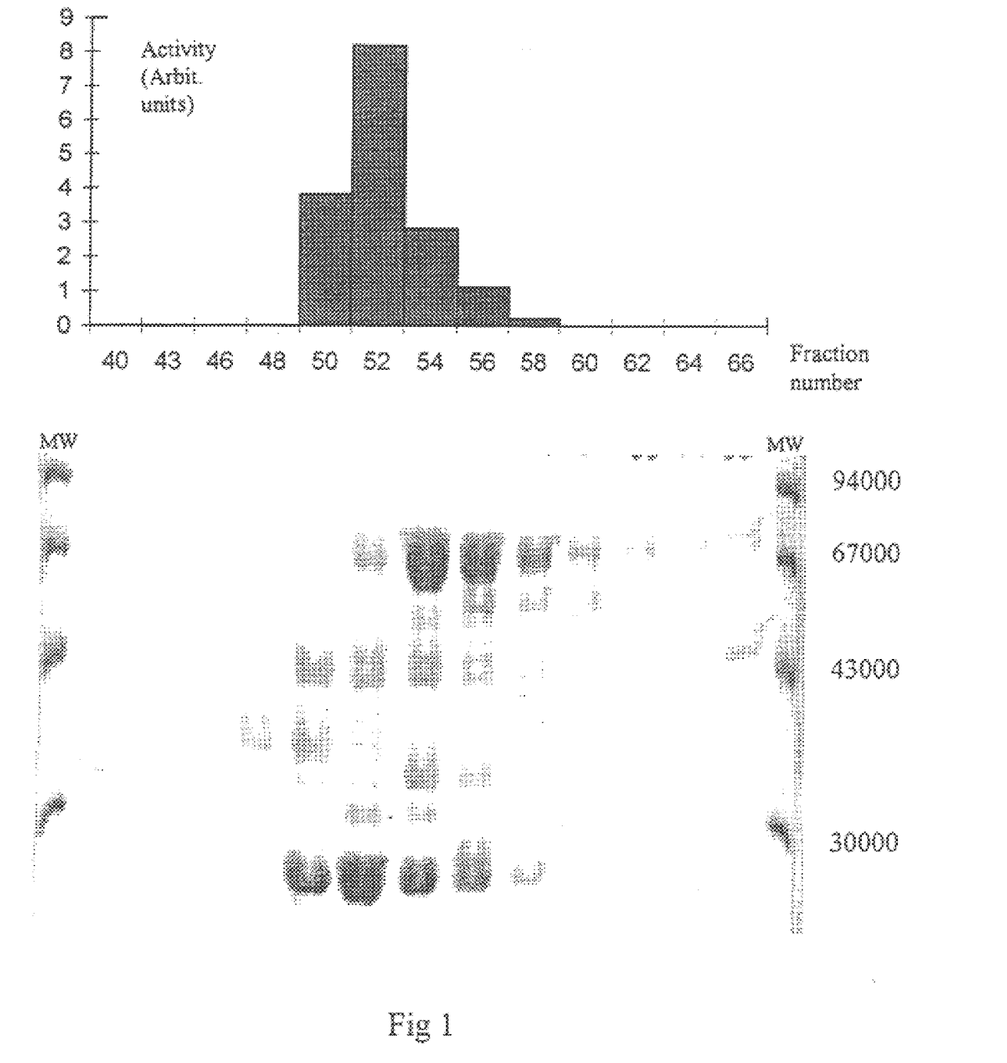
FIG. 1 shows the content of fractions eluted from the MonoQ column and the activity associated with these fractions.
Figure 2:
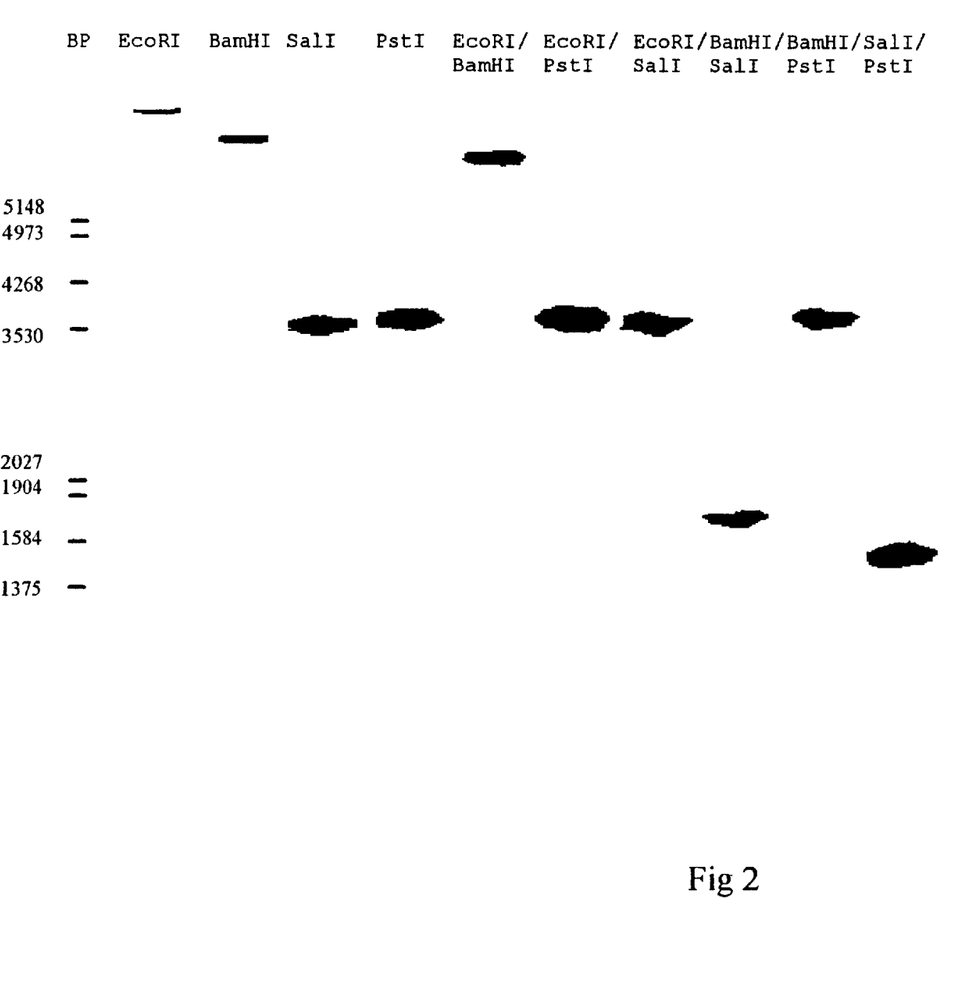
FIG. 2 shows the result of a typical Southern blotting experiment using a oligonucleotide based on the amino acid sequence of the cis-epoxysuccinate hydrolase to probe total genomic DNA of *Rhodococcus rhodochrous* LMGP-18079.

The result of a typical Southern blot experiment is shown on the FIG. 2.

Example 4

Cloning of the Cis-epoxysuccinate Hydrolase Gene
1. Construction of a Partial Gene Library About 15 μg of total chromosomal DNA of *Rhodococcus rhodochrous* are digested with the restriction enzymes BamHI and SalI. The plasmid pBluescript SK(+) (Stratagene) is digested by the same enzymes. The digested DNA is separated on a 1% agarose in TAE buffer (cf. above). Fragments of agarose corresponding to the appropriate length as determined by analysing the results of the Southern blot (1600–2200 bp) are cut off the gel. The DNA of the agarose blocks is extracted with the aid of a QIAEX II Gel extraction kit (QIAGEN) . A ligation is performed between the plasmid vector and the Rhodococcus DNA fragments and the ligation mixture is used to transform *E. coli* DH10B by electroporation using the standard protocol (Bio-Rad Gene Pulser II).

2. Cloning of the Cis-epoxysuccinate Hydrolase Gene 2.1. Cloning of an Incomplete Cis-epoxysuccinate Hydrolase Gene Transformants from step 1 are pooled in groups of ten clones. Plasmid DNA is extracted from these groups. The purified DNA is digested with the restriction enzymes BamHI and SalI and subjected to electrophoresis in agarose gel in order to perform a Southern blotting as described in example 2.

The individual clones from the positive groups are analysed again following the same protocol.

One positive clone (pREHBS) is retained for further analysis. It contains an insert with a size higher than expected (about 6.8 kb) that results from a partial digestion of the chromosomal DNA of the *Rhodococcus rhodochrous* strain.

The size of the insert is reduced, by digestion with restriction enzymes and ligation, to a length of about 1800 bp that corresponds to the expected BamHI-SalI fragment. DNA sequencing of the ends of this insert demonstrates the presence of the sequence corresponding to the oligonucleotide used to screen the library. However, it appears that the 3' end of the gene is missing.

2.2. Obtaining the Complete Gene

A partial gene library is constructed following the protocol described in 1. but using the restriction enzymes BamHI and EcoRI. This library is screened with the same oligonucleotide. A positive clone (pREHBE) is subjected to DNA sequencing on the BamHI side to confirm the overlap with the BamHI-SalI fragment.

The size of the insert of pREHBE is about 8 kb. Restriction analysis of the insert of pREHBE shows that the gene is located on a 1.4 kb SphI-XhoI fragment. To clone this fragment, the plasmid pREHBE is digested first with SphI, treated with the Klenow fragment of DNA polymerase and digested with XhoI. The fragment of interest is purified after agarose gel electrophoresis and inserted by ligation in pBluescriptSK(+) that has been digested by BamHI, treated with the Klenow fragment of DNA polymerase and digested with XhoI. The plasmid obtained is termed pREHXS and has been deposited (in *E. coli* DH10B) under the accession number LMBP-3666.

Example 5

Characterisation of the Cis-epoxysuccinate Gene

The DNA sequence of the insert of pREHXS is determined manually using the dideoxynucleotide chain-termination procedure (Sanger, F., Nickelen, S., Coulson, A. R., Proc. Nat. Acad. Sci. USA, 74, p. 5463 (1977)). Specific oligonucleotides are used as primers in the sequencing reactions. Computer analysis is done with the PC/GENE program.

The complete nucleotide sequence is determined and is given in FIG. 3 (SEQ ID NO 5).

Figure 4:
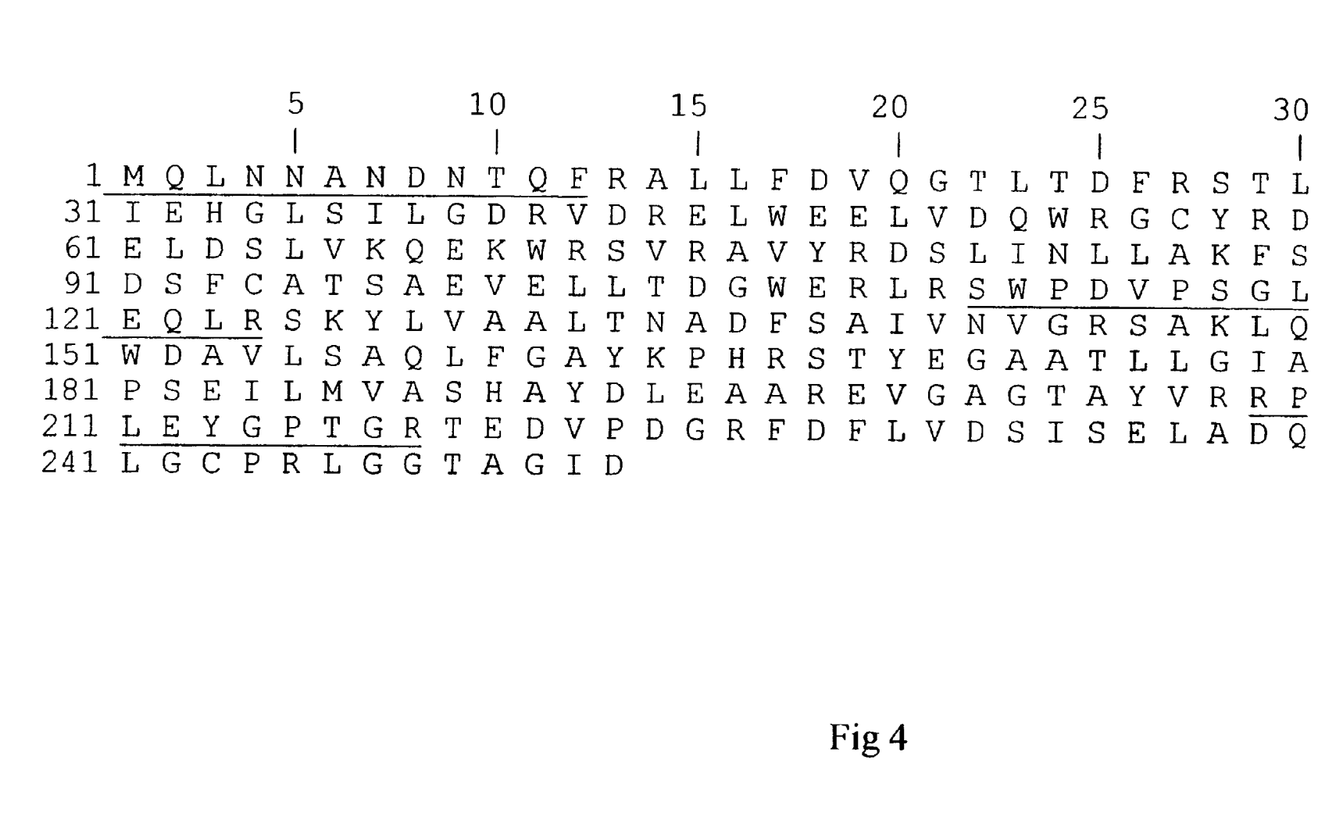
FIG. 4 shows the amino acid sequence deduced from the sequence of the *Rhodococcus rhodochrous* LMGP-18079 cis-epoxysuccinate hydrolase gene. The amino acid sequences obtained by chemical sequencing of the enzyme are underlined.

The sequence obtained comprises 1366 bp, 67 bp in the 5' non-coding region and 543 bp in the 3' non-coding region. The polypeptide derived from the coding sequence is 253 amino acids long and has a predicted molecular weight of 28 kDa. The amino acid seqence of the cis-epoxysuccinate hydrolase is given in FIG. 4 (SEQ ID No 6) The fragments of the amino acid sequence determined in example 2 are present in this sequence. SEQ ID NO 1 corresponds to the amino acids 1 to 12, SEQ ID NO 2 corresponds to the amino acids 112 to 124 and SEQ ID NO 3 corresponds to amino acids 209 to 218.

Example 6

Expression of the Cis-epoxysuccinate-hydrolase Gene in *Escherichia coli*

The *Escherichia coli* strain DH10B containing the plasmid pREHXS is cultivated overnight in 2×LB medium (Yeast Extract 1%, Bacto-tryptone 2%, NaCl 2%) supplemented with 100 μg/ml of ampicillin. The same strain with the pBluescriptSK(+) plasmid without insert is used as a control.

The activity of the cis-epoxysuccinate hydrolase is determined in the cells collected from the two cultures using the protocol described in example 1. No activity could be detected in the control. About 150 units is present in the strain expressing the cis-epoxysuccinate gene.

Example 7

Production of L-tartaric Acid 1. Enzyme Production

The *E. coli* strain containing the plasmid pREHXS is grown for 8 hours in 100 ml at 35° C. with agitation in LB medium supplemented with 100 μg/ml ampicillin. The culture is transferred in 1 liter of the same medium and cultivated again for 8 hours. This culture is used to inoculate a 15 l Braun Biostat E fermentor. After 24 hours, the culture is stopped and the cells are collected by centrifugation for 10 min. at 10000 g and 4° C. Cells are washed once with 10 mM potassium phosphate buffer pH 7.0 and centrifuged again. Finally the cells are suspended in one volume of the buffer and stored at −20° C. until use or dried by lyophilisation. The cells can also be dried by spray drying. The cells are preferably stored in closed bags or containers to protect them from humidity. Storage at lower temperature and storage under vacuum can extend the shelf life of the dried cells. In a sealed polyethylene bag the dried cells remain at 90% of their original activity after 3 months storage at ambient temperature (25° C.).

This enzymatic activity is advantageously maintained constant at a pH higher than 7, preferably at a pH comprised between 7.0 and 10, more preferably at a pH comprised between 7.5 and 9.5.

2. Bioconversion of Cis-epoxysuccinate

The bioconversion is performed in a 15 l Braun Biostat E fermentor. 10 l of a 20% cis-epoxysuccinate are mixed with 50 g of dried cells and 625 ml of a 2% (w/v) Triton X-100 solution. The pH is maintained constant at 8.0 with NaOH or HCl. The mixture is incubated under agitation (200 rpm) at 37° C. for 40 hours. The disappearance of the cis-epoxysuccinate and the synthesis of L-tartaric acid is followed by HPLC (see example 1).

A deposit has been made according to the Budapest Treaty for the micro-organisms *Rhodococcus rhodochrous* under the deposit number LMGP-18079 at the BCCM/LMG Plasmid collection, Laboratorium voor Moleculaire Biologie, Universiteit Gent, K. L. Ledenganckstraat, 35, B-9000 Gent and for *E. coli* containing the plasmid comprising the sequence according to the invention under the deposit number LMBP-3666 at the BCCM/LMBP Plasmid collection, Laboratorium voor Moleculaire Biologie, Universiteit Gent, K. L. Ledenganckstraat, 35, B-9000 Gent.

What is claimed is:

1. An isolated and purified epoxide hydrolase polypeptide encoded by a polynucleotide from Rhodococcus and having a molecular weight lower than 30 kD.

2. The epoxide hydrolase polypeptide of claim 1, wherein it presents an optimum enzymatic activity at a pH above 7.0 and 80% of the optimum enzymatic activity is obtained at a pH between 7.5 and 9.5.

3. The epoxide hydrolase polypeptide of claim 1, wherein it is intra-cellularly expressed by a recombinant host cell.

4. The epoxide hydrolase of claim 3 wherein said host cell is a bacterium or fungus.

5. The epoxide hydrolase polypeptide of claim 1, that is more than 50% homologous with SEQ ID NO 6.

6. The epoxide hydrolase polypeptide of claim 5, that is more than 70% homologous with the amino acid sequence SEQ ID NO 6.

7. The epoxide hydrolase polypeptide of claim 6, that is more than 90% homologous with the amino acid sequence SEQ ID NO 6.

8. An isolated or purified epoxide hydrolase polypeptide comprising SEQ ID NO 6 or a portion thereof that still has epoxide hydrolase enzymatic activity and a molecular weight less than 30 kD.

9. A solid support comprising the isolated and purified epoxide hydrolase of claim 1.

10. A method of hvdrolysing an epoxide, comprising treating the epoxide with the epoxide hydrolase polypeptide of claim 1.

11. The method of claim 10 wherein the epoxide is cis-epoxysuccinate.

12. An isolated and purified expoxide hydrolase polypeptide encoded by the polynucleotide of SEQ ID NO: 5 and having a molecular weight lower than 30 kD.

* * * * *

```
                         SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO: 1:

Met Gln Leu Asn Asn Ala Asn Asp Asn Thr Gln Phe
1               5                   10

(2) INFORMATION FOR SEQ ID NO: 2:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 2:

Ser Trp Pro Asp Val Pro Ser Gly Leu Glu Gln Leu Arg
1               5                   10

(2) INFORMATION FOR SEQ ID NO: 3:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (iii) HYPOTHETICAL: NO
```

(iv) ANTI-SENSE: NO (v) FRAGMENT TYPE: internal (xi) SEQUENCE DESCRIPTION: SEQ ID NO: 3:

Arg Pro Leu Glu Tyr Gly Pro Thr Gly Arg
1               5                   10

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO: 4:

AAYAAYGCNA AYGAYAAYAC                                                   20

(2) INFORMATION FOR SEQ ID NO: 5:

(i) SEQUENCE CHARACTERISTICS:
        (A) LENGTH: 1366 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

GTCTTATCCT GGTAGCGCCC GTAATTTCGT GGGCTATCTT CGTTCTTCCG AGTGGATTGT         60

GAGCACAATG CAACTGAACA ATGCGAACGA CAACACGCAG TTCCGGGCCC TGCTTTTCGA        120

CGTGCAGGGG ACTCTGACAG ATTTCCGTTC CACACTCATC GAGCACGGCT TATCGATTCT        180

CGGAGACAGA GTGGATCGAG AACTCTGGGA GGAATTGGTC GACCAATGGC GCGGCTGCTA        240

TCGAGACGAG CTCGATTCCT TGGTCAAACA GGAGAAATGG CGCTCGGTCC GCGCCGTGTA        300

CCGAGATTCT CTTATCAATC TTCTCGCAAA ATTCTCTGAC AGTTTCTGCG CCACCTCGGC        360

CGAAGTGGAA TTGCTGACCG ATGGTTGGGA ACGTCTTCGG TCGTGGCCGG ACGTCCCCTC        420

TGGATTGGAA CAGCTGCGGT CTAAGTACCT CGTCGCGGCA CTGACGAATG CGGACTTTTC        480

TGCCATCGTC AACGTCGGGC GTAGCGCCAA ACTGCAATGG GACGCTGTTC TTTCAGCTCA        540

ACTCTTTGGA GCCTACAAGC CCCACCGGTC AACATATGAG GGAGCCGCGA CACTCCTGGG        600

TATCGCTCCG TCAGAGATCC TCATGGTCGC CTCCCATGCA TACGATCTCG AAGCGGCGCG        660

GGAAGTGGGA GCCGGCACAG CGTACGTCAG ACGGCCACTG GAATACGGAC CGACGGGGCG        720

AACCGAGGAC GTTCCCGATG GACGTTTCGA TTTCTTGGTC GACAGCATCA GTGAACTGGC        780

TGATCAGCTG GGCTGCCCAC GACTCGGTGG AACTGCCGGT ATCGATTGAC ATCGACCGGC        840

GGTTCCACGC GTCCCTTGTT TTCGGTGCCT GCATTCCCCG TGACGGCAAT TCAGTCACGG        900

GGAATGCAGG CTCTGCTCTG TGCCCAGGAT TCAGGCGCT TCCCAGGCAA CTGGAGTTTT        960

TGCAGCGTAG AGGCGCGCTT CGTTCATGAG TTCCTGTGCG GGGGGTGTGA GATGACTCCG       1020

-continued

```
CCTACAGACA GCGGCGATGT GAAGGTAGGA CTCCGGGACG AATGCGGTGC ACGGTGGCGC    1080

CGACCTGCCG TGCCGATGGC GCCCAGGAGG ACGGCATGAC AGCCTGTCCG AATCCGCTGA    1140

GCACCATCGG CAGGATCGAG GTCCGGTGGG CAACTTCGGC GACGATGGTG GCTTCGACAC    1200

CGCTGGCGAG AACCTCGTCG ACCAGCGTTC GCATCAATGA TCCTCGCTGG GAGACAATCA    1260

ATCGGAAGCC GGACAGTTCC GACCGGTAAA TTTCCGGACG GTCCGGCGTC TCTGACCCGG    1320

GCCCGGACAT GAGGATCAGC GGTTGACTTT CCAGTGCCAC AACCTC                  1366
```

(2) INFORMATION FOR SEQ ID NO: 6:

(i) SEQUENCE CHARACTERISTICS:
        (A) LENGTH: 253 amino acids
        (B) TYPE: amino acid
        (C) STRANDEDNESS: single
        (D) TOPOLOGY: linear     (ii) MOLECULE TYPE: protein     (iii) HYPOTHETICAL: NO     (iv) ANTI-SENSE: NO     (xi) SEQUENCE DESCRIPTION: SEQ ID NO: 6:

```
Met Gln Leu Asn Asn Ala Asn Asp Asn Thr Gln Phe Arg Ala Leu Leu
1               5                  10                  15

Phe Asp Val Gln Gly Thr Leu Thr Asp Phe Arg Ser Thr Leu Ile Glu
            20                  25                  30

His Gly Leu Ser Ile Leu Gly Asp Arg Val Asp Arg Glu Leu Trp Glu
        35                  40                  45

Glu Leu Val Asp Gln Trp Arg Gly Cys Tyr Arg Asp Glu Leu Asp Ser
    50                  55                  60

Leu Val Lys Gln Glu Lys Trp Arg Ser Val Arg Ala Val Tyr Arg Asp
65                  70                  75                  80

Ser Leu Ile Asn Leu Leu Ala Lys Phe Ser Asp Ser Phe Cys Ala Thr
                85                  90                  95

Ser Ala Glu Val Glu Leu Leu Thr Asp Gly Trp Glu Arg Leu Arg Ser
            100                 105                 110

Trp Pro Asp Val Pro Ser Gly Leu Glu Gln Leu Arg Ser Lys Tyr Leu
        115                 120                 125

Val Ala Ala Leu Thr Asn Ala Asp Phe Ser Ala Ile Val Asn Val Gly
    130                 135                 140

Arg Ser Ala Lys Leu Gln Trp Asp Ala Val Leu Ser Ala Gln Leu Phe
145                 150                 155                 160

Gly Ala Tyr Lys Pro His Arg Ser Thr Tyr Glu Gly Ala Ala Thr Leu
                165                 170                 175

Leu Gly Ile Ala Pro Ser Glu Ile Leu Met Val Ala Ser His Ala Tyr
            180                 185                 190

Asp Leu Glu Ala Ala Arg Glu Val Gly Ala Gly Thr Ala Tyr Val Arg
        195                 200                 205

Arg Pro Leu Glu Tyr Gly Pro Thr Gly Arg Thr Glu Asp Val Pro Asp
    210                 215                 220

Gly Arg Phe Asp Phe Leu Val Asp Ser Ile Ser Glu Leu Ala Asp Gln
225                 230                 235                 240

Leu Gly Cys Pro Arg Leu Gly Gly Thr Ala Gly Ile Asp
                245                 250
```

(2) INFORMATION FOR SEQ ID NO: 7:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 7:

GTCTGCAGAG GAGGAGCACA ATGCAACTG                                29

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

AAGAATTCCT GGGCACAGAG C                                        21

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GGGATGCATA GGAGGTAACA TATGTTTAAG                                30

(2) INFORMATION FOR SEQ ID NO: 10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GGGAATTCAA TGGAAGGTGC GTTATAACG                                29

(2) INFORMATION FOR SEQ ID NO: 11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

AACTGCAGCA ATGCAACTGA ACAATGCG                                 28